United States Patent [19]

Milovac et al.

[11] Patent Number: 5,047,247
[45] Date of Patent: Sep. 10, 1991

[54] DISPERSIBLE TABLETS OF DIHYDROERGOTOXINE METHANESULFONATE AND OF ACID ADDITION SALTS THEREOF

[75] Inventors: Jenny Milovac; Mateja Kovacic, both of Ljubljana; Zdravko Kopitar, Menges; Janja Urbancic-Smerkolj; Andrej Lenardic, both of Ljubljana; Mirjan Zorz, Grosuplje; Bojan Kofler, Skofja Loka; Angela Vene-Mozina; Vida Nikolic, both of Ljubljana; Marija Lampret, Sentvid pri Sticni; Breda Meden, Ljubljana, all of Yugoslavia

[73] Assignee: LEK, Yugoslavia

[21] Appl. No.: 412,740

[22] Filed: Sep. 26, 1989

[30] Foreign Application Priority Data

Sep. 30, 1988 [YU] Yugoslavia .................... P 1839/88

[51] Int. Cl.$^5$ .................... A61K 9/20; A61K 9/14; A61K 9/50
[52] U.S. Cl. .................... 424/465; 424/464; 424/489; 424/493; 424/499; 424/501
[58] Field of Search ............... 424/464, 465, 489, 493, 424/499, 501; 514/250

[56] References Cited

U.S. PATENT DOCUMENTS 4,122,177 10/1978 Fehr .................................. 514/250

FOREIGN PATENT DOCUMENTS 1180120 2/1970 United Kingdom .

Primary Examiner—Thurman K. Page
Assistant Examiner—G. S. Kishore
Attorney, Agent, or Firm—Pollock, Vande Sande & Priddy

[57] ABSTRACT

There are described novel dispersible tablets of dihydroergotoxine or of acid addition salts thereof, containing 0.1 to 4% by weight of dihydroergotoxine or its acid addition salts, 4 to 60% by weight of one or more disintegrating agents, 0.8 to 10% by weight of an organic acid and, optionally, 0.2 to 2% by weight of an antioxidizing agent together with other common adjuvants. The process for the manufacture of dispersible tablets of dihydroergotoxine and of acid addition salts thereof is carried out on the basis of known methods by granulating the ingredients and by compressing the granulate to tablets. Dispersible tablets disintegrate within less than 1 minute when brought in contact with water at room temperature to yield a fine dispersion, which facilitates the oral application. Therefore such tablets are particularly suitable for the aged. Dispersible tablets containing dihydroergotoxine or acid addition salts thereof excell by their improved rate of dissolution and good bioavailability.

11 Claims, No Drawings

DISPERSIBLE TABLETS OF DIHYDROERGOTOXINE METHANESULFONATE AND OF ACID ADDITION SALTS THEREOF

TECHNICAL FIELD OF THE INVENTION

The invention belongs to the field of pharmaceutical industry and relates to dispersible tablets containing dihydroergotoxine (a 3:3:2:1 molar mixture of dihydroergocrystine, dihydroergocornine, dihydro-α-ergocriptine and dihydro-β-ergocriptine) in the form of both free bases and acid addition salts, such as methanesulphonate, maleate or tartrate salt. According to BAN (British Approved Name) nomenclature the generic name of dihydroergotoxine is also co-dergocrine.

The methanesulphonate salt of dihydroergotoxine is referred to in the The Merck Index, 1983, on pages 526-527 under the monographic number 3596. The pharmacological and clinical properties are described in more detail in the book by B. Berde and H. D. Schild, Springer Verlag, Berlin-Heidelberg-New York 1978.

Dihydroergotoxine is used in the treatment of cerebral insufficiency in aged patients and with cerebrovascular disorders related to hypertension as well as in the migraine prevention. The dispersible dihydroergotoxine or dihydroergotoxine methanesulphonate tablets yield—when brought in contact with water—a fine dispersion.

Further, the invention relates to a process for the manufacture of dispersible tablets of dihydroergotoxine and of acid addition salts thereof. By formulating the ergot alkaloids into dispersible tablets there is provided a new pharmaceutical form, which is, with respect to the mode of application, at the same dose preferred to the conventional tablet for oral administration or to the solution in geriatrics.

TECHNICAL PROBLEM

There exists a constant need for novel stable galenic forms on the basis of dihydroergotoxine methanesulphonate, which will possess improved biopharmaceutical properties, for the treatment of cerebrovascular insufficiency and cerebrovascular disorders in aged patients.

PRIOR ART

In the treatment of cerebral insufficiency and other cerebrovascular disorders with dihydroergotoxine methanesulphonate, the usual daily oral dosage is from 3 to 6 mg, the recommended dose being 4.5 mg, e.g. three times daily one tablet of 1.5 mg or once daily one tablet of 4.5 mg (conventional or sustained release tablets).

The active substance can also be administered in the form of a solution (drops). It is known that aqueous solutions of hydrogenated ergot alkaloids and of salts thereof are very susceptible to oxidative decomposition. It was tried to overcome this drawback by bubbling inert gases through the solutions at bottling. This procedure, however, was not satisfactory since upon the opening of the vessel the concentration of the active substance soon decreased.

From DE 25 55 481 stable solutions of hydrogenated ergot alkaloids are known. There is described the use of ethanol and propylene glycol and/or glycerine as pharmacologically acceptable mono or polyhydric alcohols containing up to 40% by weight of water for the stabilisation of pharmaceutically effective solutions of dihydroergocrystine, dihydroergocriptine and dihydroergocornine or mixtures thereof. The manufacturing of this pharmaceutical form, however, is quite exacting and requires special equipment.

When compared with the conventional oral tablets or the stabilized solutions, the dispersible tablets are better suitable, especially for aged patients, and more stable than the solutions; besides, the counting of the drops at dosing can be avoided.

In addition, the manufacture of dispersible tablets is simpler and less expensive, the production process does not require any special equipment as it is required for the manufacture of stable solutions of hydrogenated ergot alkaloids and of salts thereof and the operation is carried out at normal relative humidity.

Dispersible tablets are based on the presence of disintegrating agents having the ability to swell with water. Dispersible tablets rapidly disintegrate in water at room temperature to form a milky solution. This form of administration is particularly suitable for certain groups of patients, particularly for the aged. GB-A-2 067 900 discloses the preparation of dispersible tablets containing trimethoprim and sulphamethoxazole as active ingredients and cross-linked polyvinyl pyrrolidone as the disintegrating agent. The tablets disintegrate within less than 1 minute. A 100% dissolution of trimethoprim in 0.1N hydrochloric acid is achieved within 15 minutes.

EP-B-003 589 discloses another example of dispersible tablets containing an antacidic ingredient such as aluminium hydroxide and magnesium hydroxide together with a disintegrating agent, preferably sodium starch glycolate having a swelling capacity of between 5 and 100 ml/g.

EP-A-181 650 discloses dispersible tablets containing cyclandelate, which yield a fine dispersion when brought in contact with water of 20° C.; the tablets consist of a rapidly dispersible core containing one or more active substances, which is covered by a coating that is also rapidly dispersible. This form is particularly suitable for active ingredients that are prone to recrystallisation and/or sublimation.

DESCRIPTION OF THE SOLUTION OF THE TECHNICAL PROBLEM WITH EXAMPLES

The invention is based on the problem how to prepare novel and stable dispersible tablets containing dihydroergotoxine or acid addition salts thereof, which after contact with water at room temperature will disintegrate within less than 1 minute to yield a fine, flavoured dispersion, suitable for oral administration. The dispersible tablets possess an improved rate of dissolution and good bioavailability.

The dispersible tablets of the invention contain from 0.1 to 4% by weight of dihydroergotoxine or of its acid addition salt such as methanesulphonate as the active ingredient.

The essential ingredients imparting the desired properties to the dispersible tablets and making possible a rapid swelling and/or good wettability of the tablets and thereby a quick disintegration thereof are disintegrating agents, such as corn or potato starch or modified starches (sodium carboxymethyl starch etc.), microcrystalline cellulose, formaldehyde casein products (e.g. Esma-Spreng ®), cross-linked sodium carboxymethyl cellulose (e.g. Ac-Di-Sol ®), polyvinyl pyrrolidone (Kollidon K25 or K30) and others. It has been found that the best disintegration is achieved by a combination of two or more disintegrating agents, which are contained in the tablet in an amount from 4 to 60% by weight.

The tablets may also contain other pharmaceutically acceptable ingredients being used in the manufacture of tablets and dispersible tablets, such as binders e.g. cellulose, polyvinyl pyrrolidone, polyvinyl alcohol, starch etc., lubricating agents e.g. magnesium stearate, stearic acid, talcum, silica (Aerosil 200 V ®) etc., fillers e.g. lactose, sugar, mannitol and sorbitol, as well as flavouring and taste-improving substances e.g. sodium saccharin, Aspartame, cyclamate, menthol etc.

It is well known that ergot alkaloids and 9,10-dihydro ergot alkaloids, such as dihydroergotoxine, in free base form are poorly soluble in water and thus unsuitable for pharmaceutical uses. Their water-solubility and thereby an at least moderate resorption in the organism can be improved by converting them to their acid addition salts. These acid addition salts are known and described in the literature (e.g. The Merck Index).

It has been found that an improved rate of dissolution of dihydroergotoxine methanesulphonate from dispersible tablets and thus an improved resorption is achieved if said tablets containing from 0.8 to 10% by weight, preferably about 4% by weight of an organic acid such as citric, tartaric, malic acid etc. By this additive the solubility of the therapeutically active substance (dihydroergotoxine methanesulphonate), that is otherwise poorly soluble in water, is improved, which results in an improved and faster resorption. Preferably, citric acid is used as the organic acid.

The improved rate of dissolution of dihydroergotoxine methanesulphonate from dispersible tablets containing added organic acid in comparison with dispersible tablets that do not contain this additive or with conventional tablets is an important novelty. By including the organic acid in the composition of the dispersible tablet, there are achieved a complete dissolution and also a more pleasant taste.

Since the active substance is mainly already dissolved in water, there is excluded the possibility for any undissolved portion to remain in the glass, i.e. the whole dose is administered without fail.

Optionally, the tablet also contains 0.2 to 2% by weight of an antioxidizing agent such as butyl hydroxyanisole.

The pharmacokinetic properties of the dispersible tablet containing 4.5 mg of dihydroergotoxine methanesulphonate were evaluated by comparison with the commercial preparation (tablet) containing the same amount of the active ingredient.

In vitro tests show that the dispersible tablet dissolves in water within a very short time ($t_{90\%} = 2$ min).

In vivo tests show that the dispersible tablet has a substantially greater absorption constant ($K_a$). The times necessary to reach the maximum plasma concentrations ($t_{max}$) differ statistically significantly, too.

The tests also demonstrate an excellent bioavailability of the dispersible tablets, which in comparison with the conventional commercial preparation (tablet) amount to 113.45%.

The process for the manufacture of dispersible tablets containing dihydroergotoxine or its methanesulphonate salt is carried out in such a manner that the therapeutically active ingredient, the organic acid such as citric acid, and optionally the antioxidizing agent are first dissolved in an organic solvent such as ethanol. With the resulting solution the filler such as lactose, cellulose etc. is moistened, the dye and the sweetening agent are added thereto and a granulate is prepared. The moist granulate is passed through an oscillatory sieve, dried and again finely sieved. To the dry granulate there are added the disintegrating agent such as microcrystalline cellulose, potato or corn starch, modified starches etc. with the remaining adjuvants. The obtained mixture is passed through an oscillatory sieve and then tabletted to tablets of the desired size and shape. The thus obtained dispersible tablets disintegrate when brought in contact with water at room temperature within less than 1 minute to yield a fine dispersion suitable for therapeutical use.

The content of the dihydroergotoxine or its methanesulphonate salt in the tablet can amount to 1.0 mg, 1.5 mg, 2.0 mg, preferably 4.5 mg.

With respect to the stability, the dispersible tablets are comparable to the commercial dihydroergotoxine methanesulphonate preparation (oral tablet) and therefore the same packing material (vials, blister packs) can be used.

The invention is illustrated by the following non-limitative Examples.

EXAMPLE 1

Dispersible tablets containing 4.5 mg of dihydroergotoxine methanesulphonate (250 mg tablet)

| Ingredients | mg/tablet | % |
| --- | --- | --- |
| dihydroergotoxine methanesulphonate | 4.5 | 1.8 |
| butyl hydroxyanisole | 2.0 | 0.8 |
| microcrystalline cellulose (Avicel ® 101) | 100.0 | 40.0 |
| talcum | 7.5 | 3.0 |
| sodium saccharin | 3.0 | 1.2 |
| raspberry flavour | 3.0 | 1.2 |
| erythrosine red FDC 3 (dye) | 0.025 | 0.01 |
| sodium carboxymethyl starch (Primojel ®) | 6.00 | 2.4 |
| stearic acid | 3.00 | 1.2 |
| polyvinyl pyrrolidone (Poliplasdone XL) | 12.00 | 4.8 |
| lactose | 108.975 | 43.59 |
| Total | 250 mg | |

Method for the manufacture of 10,000 tablets

A powdery blend of lactose (1089.75 g), microcrystalline cellulose (1000 g), the dye erythrosine red FDC 3 (0.25 g) and sodium saccharin (30 g) was moistened with a solution containing dihydroergotoxine methanesulphonate (45 g) and butyl hydroxyanisole (20 g) in 80% ethanol (310 g). The moist granulate was passed through an oscillatory sieve having 1.0 to 1.2 mm openings, dried and again passed through a sieve having 0.75 mm openings. To the dry granulate there were added sodium carboxymethyl starch (60 g), polyvinyl pyrrolidone (120 g), talcum (75 g), stearic acid (30 g) and raspberry flavour (30 g) and the resulting mixture was passed through an oscillatory sieve having 0.75 mm openings. The granulate was tabletted on a rotatory tabletting machine. Thus, there were obtained round, crowned tablets weighing 250 mg, having a diameter of 9 mm, a hardnes of 39.2 to 58.8N and a friability of less than 0.5%. The hardness was tested in an Erweka TBH 28 hardness-tester and the friability was tested in an Erweka TA friability-tester.

After immersion in 100 ml of water at room temperature, the tablet disintegrated within less than 1 minute, yielding-upon stirring-a fine dispersion suitable for therapeutic application.

EXAMPLE 2

The procedure of Example 1 was followed except that 45 g of citric acid were used instead of 45 g of lactose.

EXAMPLE 3

The procedure of Example 1 was followed except that 100 g of citric acid were used instead of 100 g of lactose.

EXAMPLE 4

The procedure of Example 3 was followed except that the antioxidizing agent butyl hydroxyanisole was omitted.

PHARMACOKINETIC TESTS OF DISPERSIBLE TABLETS CONTAINING DIHYDROERGOTOXINE METHANESULPHONATE

In vitro tests

Dissolution rate of dihydroergotoxine methanesulphonate from dispersible tablets There was determined the disintegration rate of four samples of dispersible tablets containing 4.5 mg of dihydroergotoxine methanesulphonate. The composition of samples 1, 2, 3, and 4 corresponded to respective Examples 1, 2, 3 and 4.

In addition to the disintegration rate, there was tested the dissolution rate of dihydroergotoxine methanesulphonate from said samples of dispersible tablets.

Disintegration rate, release rate of dihydroergotoxine methanesulphonate from dispersible tablets The tablet was placed in a beaker containing 100 ml of water at a temperature of about 22° C. The tablet disintegrated within less that 1 minute; after stirring a homogeneous suspension was obtained. The quantities of the dissolved active substance in the test samples were determined spectrophotometrically (colour development with Van Urk reagent). The results are shown in Table 1.

TABLE 1

The percentage of dissolved dihydroergotoxine methanesulphonate in test samples

| Dispersible tablet in 100 ml water | % of dissolved dihydroegotoxine methanesulphonate | | | |
|---|---|---|---|---|
| | 1 | 2 | 3 | mean value of three tests |
| sample 1 | 53.3 | 52.6 | 54.3 | 53.4 |
| sample 2 | 81.6 | 86.9 | 82.5 | 83.7 |
| sample 3 | 90.0 | 92.4 | 91.0 | 91.1 |
| sample 4 | 89.5 | 91.7 | 90.9 | 90.7 |

For tablets containing citric acid the percentage of the dissolved active substance in the test sample was greater. Consequently, the addition of citric acid in the tablet increases the amount of dissolved dihydroergotoxine methanesulphonate in water.

DISSOLUTION RATE TEST

METHOD A

The test was performed by Paddle Method on Apparatus 2 according to USP XXI for the dissolution rate determination. The speed of the paddle was 100 rpm, the dissolution medium was 250 ml of water of a temperature of 23°±2° C. and the time of sampling was 1, 2 and 5 minutes after the start of the test.

Table 2 shows the time dependence of dihydroergotoxine methanesulphonate dissolution from 4 samples of dispersible tablets of the composition described in the respective Examples 1, 2, 3 and 4.

TABLE 2

Dissolution characteristics of dihydroergotoxine methanesulphonate from dispersible tablets in water at a temperature of 23 ± 2° C.

| | % of dissolved dihydroergotoxine methanesulphonate* + SD | | |
|---|---|---|---|
| | after 1 min | after 2 min | after 5 min |
| sample 1 | 58.3 ± 2.1 | 62.1 ± 2.2 | 63.0 ± 2.0 |
| sample 2 | 70.3 ± 2.4 | 82.9 ± 2.5 | 85.9 ± 1.8 |
| sample 3 | 80.3 ± 2.5 | 89.6 ± 2.3 | 97.2 ± 2.8 |
| sample 4 | 74.3 ± 2.5 | 87.7 ± 1.4 | 92.6 ± 1.1 |

*The results represent the mean value (n = 6).

The test results show that the dissolution rate of dihydroergotoxine methanesulphonate from a dispersible tablet with added citric acid is greater than from a tablet without added organic acid, the percentage of the dissolved active substance in the homogeneous suspension being over 70% after 1 minute and near 90% after 2 minutes. The best results were obtained with a 250 mg dispersible dihydroergotoxine methanesulphonate tablet containing 10 mg of citric acid (4% of the composition of the tablet), where practically the whole active substance is dissolved in the homogeneous suspension within 5 minutes.

METHOD B

The test was performed on Apparatus 2 according tu USP XXI for the determination of dissolution rates. The speed of the stirrer was 50 rpm, the dissolution medium was 500 ml of water of a temperature of 37°±0.5° C., the distance between the lower edge of the stirrer and the bottom of the vessel was 4.5±0.5 cm, the time of sampling was 5, 15 and 30 minutes after the start of the test.

USP XXI United States Convention (1985), p. 384-385 requires that—when testing oral tablets of dihydroergotoxine methanesulphonate—at least 75% (Q) of dihydroergotoxine methanesulphonate should dissolve within 30 minutes.

>>FDA Memorandum Aug. 17, 1974 Proposed Dissol. Studies for Dihydroergotoxine Methanesulphonate Tablets<< requires that at least 50% of dihydroergotoxine methanesulphonate should dissolve within 15 minutes and at least 80% within 30 minutes.

There were compared the dissolution rates of dihydroergotoxine methanesulphonate from 250 mg dispersible tablets containing 10 mg of citric acid (sample 3) in addition to 4.5 mg of dihydroergotoxine methanesulphonate and from a commercial preparation of dihydroergotoxine methanesulphonate (oral tablets containing 4.5 mg of dihydroergotoxine methanesulphonate, Redergin ®, produced by LEK, Ljubljana). The results are shown in Table 3.

TABLE 3

Dissolution rate of dihydroergotoxine methanesulphonate from dispersible tablets (sample 3) and from the commercial preparation Redergin ®

| | % of dissolved dihydroergotoxine methanesulphonate | | | |
|---|---|---|---|---|
| | dispersible tablet (sample 3) | | commercial preparation (Redergin ®) | |
| tablet | after 5 min | after 15 min | after 15 min | after 30 min |
| 1 | 95.0 | 99.4 | 60.8 | 91.2 |
| 2 | 89.2 | 95.7 | 55.6 | 81.5 |
| 3 | 93.8 | 99.4 | 52.1 | 84.2 |
| 4 | 94.4 | 101.3 | 66.6 | 85.6 |
| 5 | 97.9 | 98.4 | 82.8 | 97.8 |
| 6 | 95.0 | 101.1 | 57.3 | 81.5 |
| mean value ± SD | 94.2 ± 2.83 | 99.2 ± 2.05 | 62.5 ± 11.1 | 86.5 ± 6.4 |

The test results serve only for the comparison of the two different forms, they are, however, of no practical value since the dispersible tablets are not dissolved at 37° C.

IN VIVO TESTS

A comparison of bioavailability and of other pharmacokinetic parameters of dihydroergotoxine methanesulphonate after the administration of the dispersible tablet and of a commercial preparation Dispersible tablets containing 4.5 mg of dihydroergotoxine methanesulphonate and 10 mg of citric acid (sample 3) were tested in vivo in comparison with a commercial preparation (oral tablets Redergin ®-LEK, Ljubljana, containing 4.5 mg of dihydroergotoxine methanesulphonate) in order to evaluate the pharmacokinetic properties of the dispersible tablet. Both preparations were administered to 8 healthy persons of both sexes, aged from 22 to 39, having a body weight from 58 to 77 kg, to whom both preparations were given in randomized, cross-over trials in one week's interval. Blood samples were taken immediately before and 10, 20, 40, 60, 80 and 100 minutes and 2, 3, 4, 6, 8, 12 and 24 hours after the administration. The taken samples were centrifuged for 15 minutes at 3000 rpm and the pipetted-off plasma was kept in a freezer up to the analysis of the plasma concentrations of dihydroergotoxine methanesulphonate by the HPLC (High Performance Liquid Chromatography) method.

The results are shown in Table 4 and in Graph I.

TABLE 4

| | Dispersible tablet (sample 3) (containing 4.5 mg of dihydroergotoxine methanesulphonate and 10 mg of citric acid) | Commercial preparation (oral tablet containing 4.5 mg of dihydroergotoxine methanesulphonate) |
|---|---|---|
| $C_{max}$ | 0.51 ± 0.13 (ng/ml) | 0.49 ± 0.11 (ng/ml) |
| $t_{max}$ | 0.67 ± 0.18 (h) | 0.92 ± 0.29 (h) |
| $AUC^{0-T}$ | 2.38 ± 1.06 (ng.h/ml) | 2.09 ± 0.46 (ng.h/ml) |
| $K_{el}$ | 0.116 ± 0.066 (h$^{-1}$) | 0.118 ± 0.052 (h$^{-1}$) |
| $t_{\frac{1}{2}el}$ | 8.33 ± 4.73 (h) | 6.92 ± 3.01 (h) |
| $K_a$ | 2.803 ± 0.318 (h$^{-1}$) | 1.888 ± 0.482 (h$^{-1}$) |
| $C_{max}$: | maximum plasma concentration | |
| $t_{max}$: | time necessary to reach the maximum plasma concentration | |
| $AUC^{0-T}$: | area under the plasma concentration time curve up to the time of 24 hours | |
| $K_{el}$: | elimination rate constant | |
| $t_{\frac{1}{2}el}$: | biological half-life | |
| $K_a$: | absorption constant | |

When comparing the two preparations, there were found statistically significant differences for the time necessary to reach the maximum plasma concentration and for the absorption constant.

The relative bioavailability of the dispersible dihydroergotoxine methanesulphonate tablet is 113.45% as compared with the commercial oral tablet.

We claim:

1. A water-dispersible tablet of dihydroergotoxine methanesulfonate comprising
   0.1 to 4% (w/w) of dihydroergotoxine methanesulfonate as an active ingredient,
   one or more disintegrating agents in an amount from 4 to 60% (w/w) selected from the group consisting of starch, modified starch, formaldehyde casein product, microcrystalline cellulose, cross-linked carboxymethyl cellulose, and cross-linked polyvinyl pyrrolidone,
   an organic acid in an amount of from 0.8 to 10% (w/w) selected from the group consisting of citric acid, tartaric acid and malic acid, and
   0.2 to 2% by weight of butyl hydroxyanisole, as the antioxidizing agent.

2. A water-dispersible tablet according to claim 1, wherein the disintegrating agents are contained in an amount of 40 to 60% (w/w).

3. A water-dispersible tablet according to claim 2 wherein at least two disintegrating agents are present.

4. A water-dispersible tablet according to claim 1 wherein said organic acid is citric acid in an amount of about 4%.

5. A water-dispersible tablet according to claim 1, wherein the tablet contains an effective binding amount of a binder selected from the group consisting of cellulose, polyvinyl pyrrolidone, polyvinyl alcohol, and starch.

6. A water-dispersible tablet according to claim 1, wherein the tablet contains an effective flavoring or taste-improving amount of a flavoring or taste-improving agent selected from the group consisting of sodium saccharin, aspartame, cyclamate and menthol.

7. A water-dispersible tablet according to claim 1, wherein the tablet contains an effective lubricating amount of a lubricating agent selected from the group consisting of magnesium stearate, stearic acid, talcum and silica.

8. A water-dispersible tablet according to claim 1, wherein the tablet contains an effective filler amount of a filler selected from the group consisting of lactose, sugars, mannitol and sorbitol.

9. A water-dispersible tablet according to claim 1 wherein at least two disintegrating agents are present.

10. A water-dispersible tablet according to claim 1, wherein said one or more disintegrating agents comprise a mixture of microcrystalline cellulose, sodium carboxymethyl starch and cross-linked polyvinyl pyrrolidone.

11. A water-dispersible tablet according to claim 1, wherein said acid is contained in an amount of about 4% (w/w).

* * * * *